(12) United States Patent
Goi

(10) Patent No.: US 8,297,399 B2
(45) Date of Patent: Oct. 30, 2012

(54) SAFETY MANAGEMENT SYSTEM

(75) Inventor: Kouichi Goi, Kawasaki (JP)

(73) Assignee: Laurel Precision Machines Co., Ltd., Osaka-shi (JP)

( * ) Notice: Subject to any disclaimer, the term of this patent is extended or adjusted under 35 U.S.C. 154(b) by 144 days.

(21) Appl. No.: 12/149,897

(22) Filed: May 9, 2008

(65) Prior Publication Data

US 2008/0289895 A1  Nov. 27, 2008

(30) Foreign Application Priority Data

May 23, 2007  (JP) ................ P2007-136579

(51) Int. Cl.
- B60K 28/06 (2006.01)
- G01N 33/49 (2006.01)
- G01N 33/66 (2006.01)
- G01N 33/68 (2006.01)

(52) U.S. Cl. ....... 180/272; 340/576; 340/5.82; 600/322; 701/1

(58) Field of Classification Search ............ 180/272; 340/576, 5.82; 382/115; 600/310, 322, 326, 600/328; 701/1; 702/19; 713/186
See application file for complete search history.

(56) References Cited

U.S. PATENT DOCUMENTS

| | | | |
|---|---|---|---|
| 3,508,830 A | 4/1970 | Hopkins et al. | |
| 4,035,083 A | 7/1977 | Woodriff et al. | |
| 5,303,575 A | 4/1994 | Brown et al. | |
| 5,589,045 A | 12/1996 | Hyodo | |
| 5,719,950 A * | 2/1998 | Osten et al. ................ 382/115 |
| 6,097,480 A | 8/2000 | Kaplan | |
| 6,216,032 B1 | 4/2001 | Griffin et al. | |
| 6,229,908 B1 * | 5/2001 | Edmonds et al. ............. 382/124 |
| 6,313,749 B1 * | 11/2001 | Horne et al. .................. 340/575 |
| 6,726,636 B2 | 4/2004 | Der Ghazarian et al. | |
| 6,748,301 B1 * | 6/2004 | Ryu .................................. 701/1 |
| 6,886,653 B1 | 5/2005 | Bellehumeur | |
| 7,103,460 B1 | 9/2006 | Breed | |
| 7,203,345 B2 * | 4/2007 | Rowe et al. .................... 382/115 |
| 7,248,905 B2 * | 7/2007 | Fukuda et al. ................ 600/310 |
| 7,386,152 B2 * | 6/2008 | Rowe et al. .................. 382/124 |
| 7,885,434 B2 | 2/2011 | Kitane et al. | |
| 7,913,090 B2 | 3/2011 | Abe | |

(Continued)

FOREIGN PATENT DOCUMENTS

EP  1 703 045 A1  9/2006

(Continued)

OTHER PUBLICATIONS

Non-Final Rejection mailed Jun. 3, 2011 in co-pending U.S. Appl. No. 12/149,719 (13 pages).

(Continued)

*Primary Examiner* — Joseph Rocca
*Assistant Examiner* — Keith Frisby
(74) *Attorney, Agent, or Firm* — Nixon & Vanderhye P.C.

(57) ABSTRACT

The safety management system of the present invention includes: a driver authentication section which authenticates a driver of a transportation machine and outputs an authentication result; a health status determination section which measures blood component data of a driver authenticated by the driver authentication section, determines a health status of the driver from the blood component data, and outputs a determination result; and a motive power control section which permits or prohibits operation of the transportation machine by controlling motive power of the transportation machine based on the authentication result and the determination result.

7 Claims, 2 Drawing Sheets

U.S. PATENT DOCUMENTS

| | | | |
|---|---|---|---|
| 2002/0084130 A1* | 7/2002 | Der Ghazarian et al. | 180/272 |
| 2003/0084288 A1 | 5/2003 | de Jong et al. | |
| 2003/0084302 A1 | 5/2003 | de Jong et al. | |
| 2003/0100841 A1 | 5/2003 | Griffin et al. | |
| 2003/0204290 A1 | 10/2003 | Sadler et al. | |
| 2004/0035423 A1 | 2/2004 | Platt et al. | |
| 2004/0039297 A1* | 2/2004 | Abreu | 600/558 |
| 2004/0220483 A1 | 11/2004 | Yeo et al. | |
| 2004/0240712 A1 | 12/2004 | Rowe et al. | |
| 2005/0087382 A1 | 4/2005 | Bellehumeur | |
| 2005/0192493 A1* | 9/2005 | Wuori | 600/322 |
| 2005/0254690 A1 | 11/2005 | Nagasaka et al. | |
| 2005/0275550 A1 | 12/2005 | Wang et al. | |
| 2005/0286744 A1 | 12/2005 | Yoshizu et al. | |
| 2006/0023919 A1 | 2/2006 | Okamura et al. | |
| 2006/0048212 A1 | 3/2006 | Tsuruoka et al. | |
| 2006/0072793 A1 | 4/2006 | Determan | |
| 2006/0078170 A1 | 4/2006 | Kamata et al. | |
| 2006/0080547 A1 | 4/2006 | Higashiura et al. | |
| 2006/0180371 A1 | 8/2006 | Breed et al. | |
| 2006/0217615 A1 | 9/2006 | Huiku et al. | |
| 2006/0224171 A1* | 10/2006 | Sakata et al. | 606/181 |
| 2006/0284839 A1 | 12/2006 | Breed et al. | |
| 2007/0003112 A1 | 1/2007 | Awatsu et al. | |
| 2007/0037554 A1 | 2/2007 | Freeny | |
| 2007/0067330 A1 | 3/2007 | Hernandez et al. | |
| 2007/0092924 A1* | 4/2007 | Anderson | 435/23 |
| 2007/0260887 A1 | 11/2007 | Ito | |
| 2008/0176305 A1 | 7/2008 | Sato et al. | |
| 2009/0240119 A1 | 9/2009 | Schwaibold et al. | |
| 2010/0008545 A1 | 1/2010 | Ueki et al. | |
| 2010/0010689 A1 | 1/2010 | Yasushi et al. | |

FOREIGN PATENT DOCUMENTS

| | | |
|---|---|---|
| JP | 2001-258867 | 9/2001 |
| JP | 2002-172105 | 6/2002 |
| JP | 2003-146107 | 5/2003 |
| JP | 2005-202899 | 7/2005 |
| JP | 2006-6762 | 1/2006 |
| JP | 2006-248254 | 9/2006 |
| JP | 2006-291604 | 10/2006 |
| JP | 2007-23526 | 2/2007 |
| JP | 2007-097820 | 4/2007 |
| JP | 2007-117221 | 5/2007 |
| TW | I254254 | 5/2006 |
| WO | WO 99/32317 | 7/1999 |
| WO | DE 202005020535 U1 | 4/2006 |
| WO | WO 2008/019800 A1 | 2/2008 |

OTHER PUBLICATIONS

Non-Final Rejection Nov. 28, 2011, in co-pending U.S. Appl. No. 12/149,719 (14 pages).

Office Action dated Oct. 4, 2011, issued in Japanese Patent Application No. 2007-136579, with English Translation (6 pgs).

Office Action dated Nov. 22, 2011 issued in Japanese Patent Application No. 2007-139197, with English Translation (4 pages).

Notice of Allowance dated May 29, 2012 issued in Japanese Patent Application No. 2007-136579, 6 pp.

Office Action dated Feb. 16, 2012, issued in Taiwanese Patent Application No. 097117333, with English Translation, 7 pp.

Final Office Action dated Apr. 30, 2012 issued in co-pending U.S. Appl. No. 12/149,719, 15 pp.

* cited by examiner

SAFETY MANAGEMENT SYSTEM

BACKGROUND OF THE INVENTION

1. Field of the Invention

The present invention relates to a safety management system which permits or prohibits operation by controlling the motive power of transportation machines such as a vehicle, a ship, an aircraft, a train, and so forth.

Priority is claimed on Japanese Patent Application No. 2007-136579, filed May 23, 2007, the contents of which are incorporated herein by reference.

2. Description of the Related Art

Japanese Unexamined Patent Application, First Publication No. 2006-248254 discloses a safety management system which can prohibit operation by authenticating a driver of a transportation machine, and in the case where the alcohol concentration detected from the driver exceeds a predetermined threshold, restricts starting of the engine of the transportation machine.

There is a need to construct a safety management system which can authenticate the health status of a driver which has an influence on the operation of the transportation machines, so that the authentication results can reflect on regulation of operation of the transportation machines.

SUMMARY OF THE INVENTION

An object of the present invention is to provide a safety management system that controls the motive power of transportation machines to thereby permit or prohibit the operation thereof, in which the health status of the driver is reflected on to control the motive power.

In order to solve the above problem, the safety management system of the present invention comprises: a driver authentication section which authenticates a driver of a transportation machine and outputs an authentication result: a health status determination section which measures blood component data of a driver authenticated by the driver authentication section, determines a health status of the driver from the blood component data, and outputs a determination result; and a motive power control section which permits or prohibits operation of the transportation machine by controlling motive power of the transportation machine based on the authentication result and the determination result.

In the safety management system of the present invention, the motive power control section may control starting of an engine of the transportation machine, based on the authentication result and the determination result.

According to this configuration, a legitimate driver is authenticated. Furthermore based on the blood component data of that driver, it is determined whether or not the health status of a driver is favorable. Based on the results, operation can be permitted or prohibit by controlling starting of the engine of the transportation machines.

In the safety management system of the present invention, the motive power control section may control the motive power of the transportation machine according to whether or not values of each of items of the blood component data are within predetermined ranges.

In the safety management system of the present invention, the motive power control section may control the motive power of the transportation machine according to whether or not values of each of specific items of the items of the blood component data are within predetermined ranges.

In the safety management system of the present invention, the motive power control section may control the motive power of the transportation machine according to a number of items within the predetermined ranges of each of the items of the blood component data.

In the safety management system of the present invention, the driver authentication section may authenticate the driver based on a vein pattern obtained by irradiating infrared rays onto a body of the driver.

According to this configuration, authentication can be performed with similar accuracy to authentication using fingerprint or iris recognition.

In the safety management system of the present invention, the health status determination section may measure the blood component data based on an absorption spectrum obtained by irradiating infrared rays onto a body of the driver.

According to this configuration, because blood component data is measured in a non-invasive manner, the physical and mental stress experienced by the driver can be minimized.

In the safety management system of the present invention, a vein pattern used by the driver authentication section and an absorption spectrum used by the health status determination section may be detected by the same sensor section.

According to this configuration, driver authentication and health status determination can be performed in the same operation, and the structure of the overall system can be simplified.

According to the present invention, a legitimate driver is authenticated, the health status of the driver is determined based on blood component data of the driver, and operation of the transportation machines is permitted or prohibited based on the results. Therefore, the likelihood of occurrence of an accident due to poor health of the driver, can be reduced.

DETAILED DESCRIPTION OF THE INVENTION

As follows is a description of an embodiment of the present invention with reference to the drawings.

Figure 1:
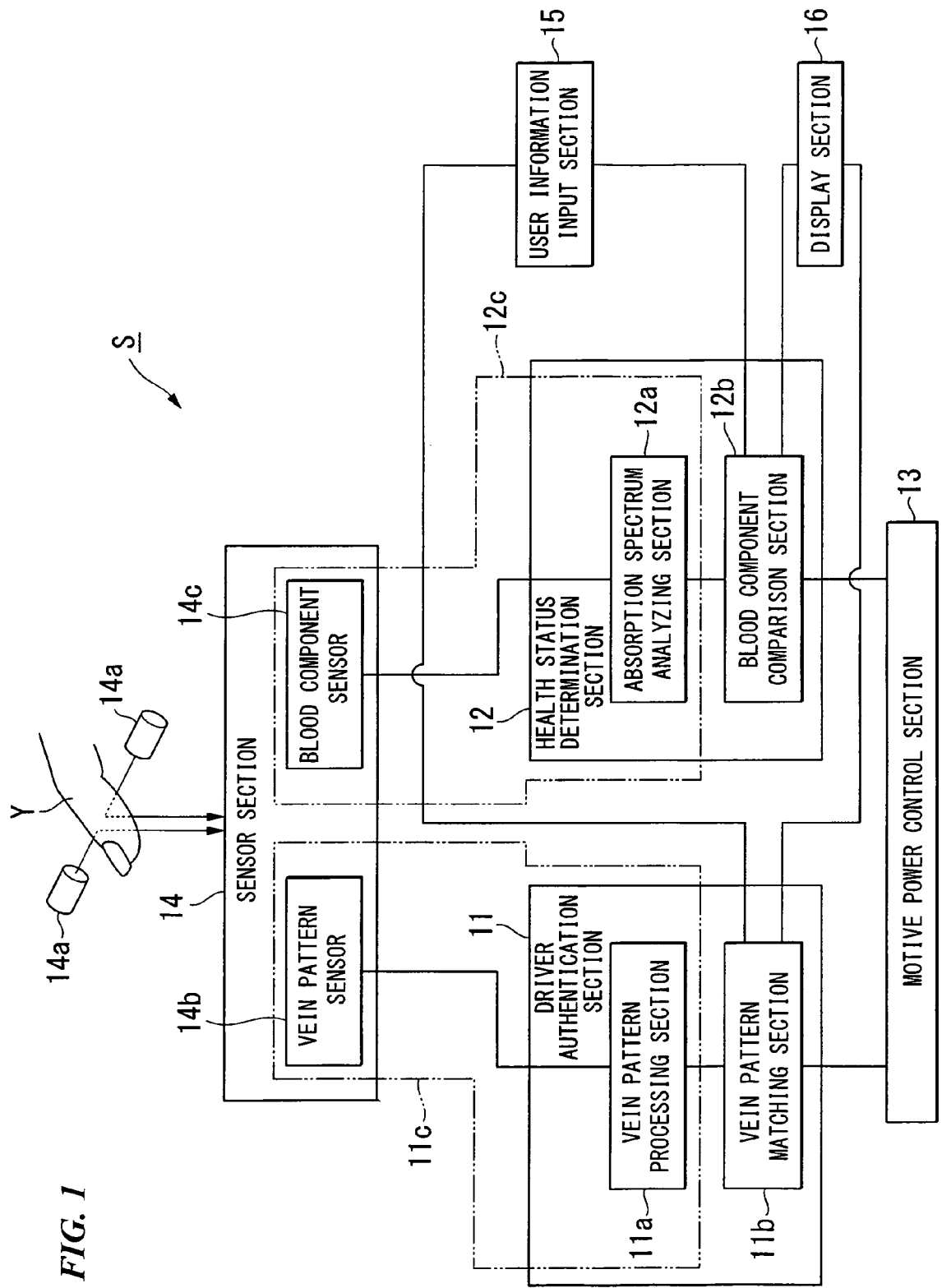
FIG. 1 is a block diagram showing a safety management system according to an embodiment of the invention.

A safety management system S shown in FIG. 1 is used for example on transportation machines such as a bus with an engine (internal combustion engine) as a prime-mover. The safety management system S performs authentication to determine whether a user (driver) is a pre-registered user, and also checks the health status of the driver. Based on the results, the safety management system S controls the motive power to thereby permit or prohibit operation of the transportation machines by the driver.

The safety management system S includes a driver authentication section 11, a health status determination section 12, and a motive power control section 13. The driver authentication section 11 performs authentication to determine whether or not a user is a legitimate driver. The health status determination section 12 determines the health status of the user from the blood component data of the user. The motive power control section 13 controls the motive power of the transportation machines based on the authentication result of the driver authentication section 11 and the judgment result of the health status determination section 12. The driver authentication section 11, the health status determination section 12, and the motive power control section 13 are formed inside an electronic control unit which controls starting and the like of the engine of the transportation machines.

The driver authentication section 11 is a known vein authentication device. The driver authentication section 11 acquires a vein pattern from, for example, the fingertip of the user, and matches the vein pattern to a pre-registered vein pattern. The driver authentication section 11, based on the results of the matching process, determines whether or not the user is permitted to operate the transportation machine, that is, the authentication section 11 determines whether the user is a legitimate driver. The vein pattern is acquired, for example, in the following manner. A user places his or her fingertip Y on a sensor section 14 positioned near the driving seat of the transportation machine. An infrared LED 14a irradiates near-infrared light onto the fingertip Y, and the reflected light is received by an imaging element such as a CCD (charge coupled device). A vein pattern processing section 11a of the driver authentication section 11 performs predetermined image processing of the signal from the imaging element. This vein pattern processing section 11a and a vein pattern sensor section 14b of the sensor section 14 constitute a vein pattern capture section 11c in the driver authentication section 11.

A user information input section 15 is a keyboard or card reader or the like. A vein pattern matching section 11b of the driver authentication section 11, based on information from the user information input section 15, retrieves a pre-registered vein pattern of the driver.

The vein pattern matching section 11b compares the retrieved vein pattern with the vein pattern obtained by the sensor section 14. If the vein pattern matching section 11b determines that the two vein patterns are the same, the user is authenticated as a legitimate driver (in which case the "authentication result is OK"). On the other hand, if the vein pattern matching section 11b determines that the two vein patterns are not the same, the user is not authenticated as a legitimate driver (in which case the "authentication result is NG"). These authentication results are displayed to the user on a predetermined display section 16 such as an LCD (liquid crystal display). A configuration may also be used in which the user information input section 15 is not provided, and driver authentication is performed by automatically comparing the vein pattern acquired by the sensor section 14 with pre-registered vein patterns.

As the health status determination section 12, a known non-invasive blood component measuring device is used. The health status determination section 12 analyzes an absorption spectrum obtained from transmitted or reflected light obtained by irradiating near-infrared rays onto the fingertip Y of the user by means of an infrared LED 14a of the sensor section 14. From the results of analyzing this absorption spectrum, the health status determination section 12 acquires data (blood component data) related to the blood components of that user. An absorption spectrum analyzing section 12a of the health status determination section 12 performs analysis of the absorption spectrum. This absorption spectrum analyzing section 12a and a blood component sensor 14c of the sensor section 14 constitute a blood component measuring section 12c in the health status determination section 12. The blood component measuring section 12c utilizes an infrared spectrophotometer.

Items of blood components measured by the health status determination section 12 include blood sugar levels, levels of enzymes such as GPT (glutamic pyruvic transaminase), levels of plasma proteins such as albumin, and cholesterol levels and lactic acid levels.

A blood component comparison section 12b of the health status determination section 12 retrieves blood component data values (the "predetermined ranges" mentioned below) registered in advance for each item of the blood data, which indicate the appropriate health status for the driver.

The blood component comparison section 12b compares the retrieved blood component data values with the blood component data obtained by analyzing the absorption spectrum. From the comparison results, the blood component comparison section 12b then determines whether the health status of the user is suitable for operating the transportation machines.

Specifically, the blood component comparison section 12b pre-designates several items in the blood component data as the specific items. The specific items are, for example, the plasma protein level and the lactic acid level which indicate the level of tiredness of the user. The blood component comparison section 12b determines whether or not the values of the specific items in the measured blood component data are within the value of the retrieved blood component data, that is, the blood component comparison section 12b determines whether the values are within the predetermined ranges for each of the specific items. These predetermined ranges are ranges whereby a determination can be made as to whether the health status of the user is appropriate for operating the transportation machines. These predetermined ranges can be set appropriately based on the age and gender of the user as well as individual differences. A construction may be employed in which the predetermined ranges are appropriately corrected or updated based on blood component data acquired in the past.

If the blood component comparison section 12b determines that the values of all the specific items are within their predetermined ranges (all items meet the required standard), the health status of the user is determined to be suitable for operating the transportation machines, that is, the health status of the user is determined to be favorable (in which case the "authentication result is OK"). On the other hand, if the blood component comparison section 12b determines that the value of one or more of the specific items is outside the predetermined range defined for the item (at least one item does not meet the required standard), the health status of the user is determined to not be suitable for operating the transportation machines, that is, the health status of the user is determined to not be favorable (in which case the "authentication result is NG"). These determination results are displayed to the user on the display section 16.

The motive power control section 13 manages whether or not to operate the transportation machine by controlling for example whether or not to start the engine serving as the prime mover of the transportation machine. Specifically, when the authentication result of the driver authentication section 11 and the judgment result of the health status determination section 12 are both OK, the motive power control section 13 permits starting of the engine by permitting operation of for example the engine starting device of the starter motor. On the other hand, if at least either the authentication result of the user authentication section 11 or the judgment result of the health status determination section 12 is NG, the motive power control section 13 for example renders the engine starting device inoperable, to thereby restrict engine starting. Although the engine starting may be restricted, it is desirable to permit the user to lock the driver compartment door or unlock the door, and to permit use of electronic equipment such as the air-conditioning and the navigation system.

In this manner, by authenticating a driver and also determining the health status of the driver, and controlling whether or not to let the driver drive the transportation machine according to the results, users other than a driver who has been granted permission in advance are prevented from driving the transportation machines, and the occurrence of accidents due to poor health of the driver can be prevented beforehand. As a method for restricting operation of the transportation machines, as well as restricting starting of the engine, for example it is possible to limit the operation or actuation of the accelerator or transmission, or limit the su power to the prime mover.

Figure 2:
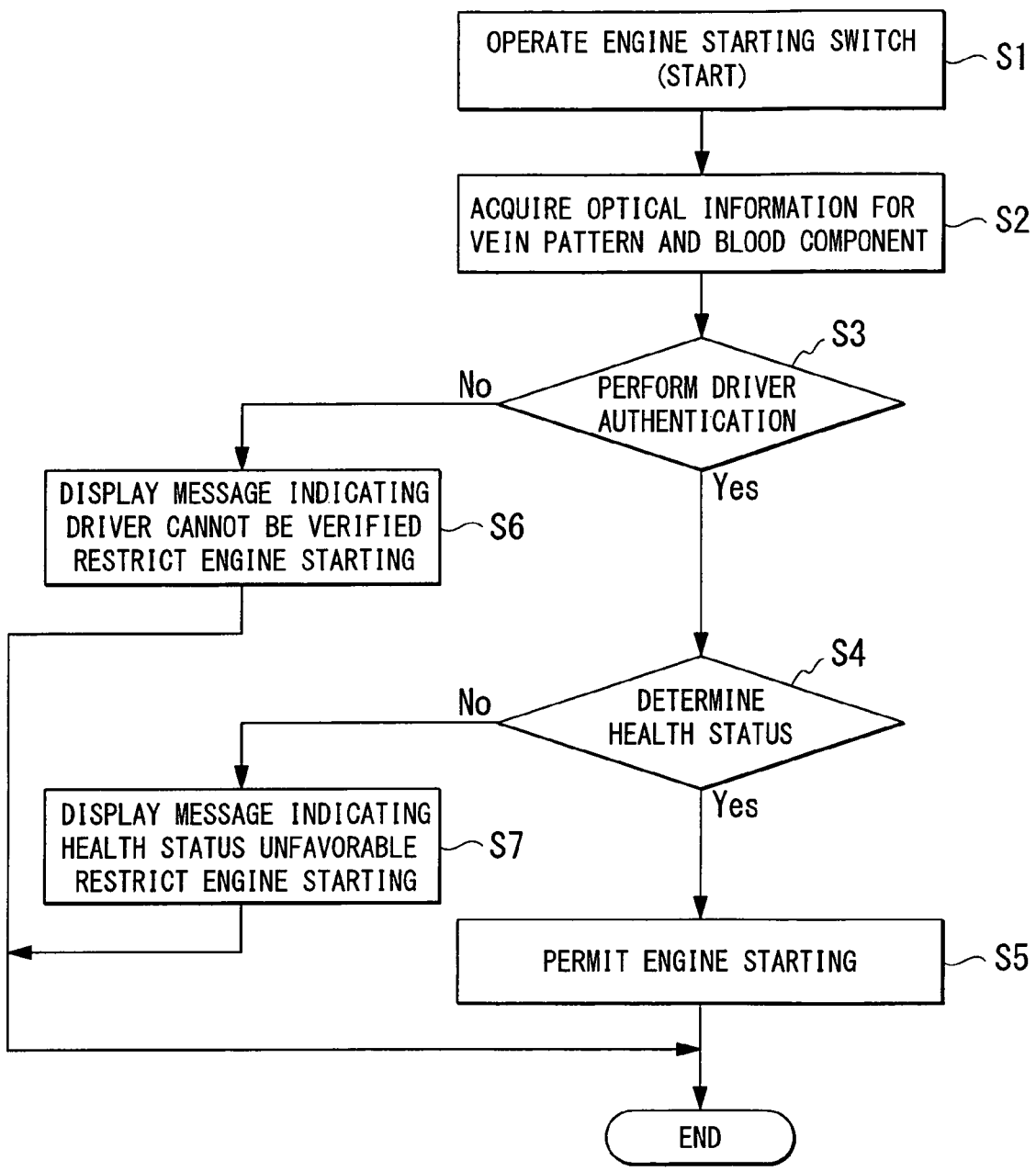
FIG. 2 is a flowchart showing the process flow of the safety management system shown in FIG. 1.

The main process flow for when the safety management system S is applied to a vehicle such as a bus equipped with an engine, is described with reference to FIG. 2. The safety management system S is not limited to a vehicle equipped with an engine, and can also be applied to various transportation machines such as a ship, an aircraft, a train, and so forth.

First, the process flow starts when a user (a driver) who gets on to the vehicle operates the engine starting switch inside the vehicle (step S1). The engine starting switch is, for example, a push-button switch, on the top face of which the user places his or her fingertip. A pair of infrared LEDs 14a are provided on either side of the engine starting switch so as to face each other. This engine starting switch and the infrared LEDs 14a constitute the sensor section 14. The engine starting switch also incorporates a light receiving section. By receiving the light emitted by the LEDs 14a after the light has passed through the fingertip Y of the user, the light receiving section acquires optical information related to the vein pattern of the fingertip Y of the user and the blood component data of the user (step S2). The engine starting switch incorporates the vein pattern sensor 14b and the blood component sensor 14c of the sensor section 14.

The vein pattern processing section 11a subjects the optical information acquired by the vein pattern sensor section 14b to predetermined image processing. Next, the vein pattern matching section 11b matches the image processed optical information to a pre-registered vein pattern. Specifically, the driver authentication section 11 compares the vein pattern acquired by the sensor section 14 with a retrieved vein pattern. Based on the results of the comparison, the driver authentication section 11 determines whether or not the user is a person who has permission, that is, the driver authentication section 11 determines whether the user is a legitimate driver (step S3).

If a determination is made that the user is a person who has permission, that is, if the authentication result is OK (YES in step S3), the processing proceeds to step S4. On the other hand, if a determination is made that the user is a person who does not have permission, that is, if the authentication result is NG (NO in step S3), the processing proceeds to step S6. In step S6, a message indicating that the user cannot be verified is displayed on the display section 16, and the motive power control section 13 performs control to restrict engine starting such as by not allowing operation of the engine starting device, that is, the motive power control section 13 controls motive power to prohibit operation of the vehicle.

In step S4, the absorption spectrum analyzing section 12a subjects the optical information acquired by the blood component sensor 14c to predetermined analysis, and the blood component comparison section 12b then compares the results of the analysis with pre-registered blood component data. Specifically, the health status determination section 12 compares the values of blood component data acquired by the sensor section 14 and retrieved blood component data. Based on the comparison results, the health status determination section 12 determines whether or not the health status of the user is suitable for operating the vehicle.

If a determination is made that the health status of the user is favorable, that is, if the judgment result is OK (YES in step S4), the processing proceeds to step S5. On the other hand, if a determination is made that the health status of the user is not favorable, that is, if the judgment result is NG (NO in step S4), the processing proceeds to step S7. In step S7, a message indicating that the health status of the user is not favorable is displayed on the display section 16, and the motive power control section 13 performs control to restrict engine starting in the manner previously described.

In step S5, the motive power control section 13 performs control to permit starting of the engine, that is, the motive power control section 13 controls motive power to permit operation of the vehicle, so that the user can operate the vehicle.

Although two infrared LEDs 14a are used in FIG. 1, a construction in which one infrared LED 14a is used may be employed. The engine starting switch may be a lever or dial instead of a push-button switch. A construction may be used in which the engine starting switch is rendered operable after the user has been authenticated and a health status determination has been performed. In this construction, the engine starting switch may be rendered operable only when the authentication result of the driver authentication section 11 and the judgment result of the health status determination section 12 are both OK, that is, the engine starting switch is rendered inoperable when any one of the authentication result and the judgment result are NG).

The sensor section 14 and the engine starting switch may be provided as separate components. For example, the sensor section 14 may be provided integral with the steering wheel or the like. A construction may also be used in which the user places his or her fingertip Y in a predetermined enclosure to allow the sensor section 14 to capture a vein pattern and acquire blood component data. The sensor section 14 may capture a vein pattern and acquire blood component data of the user using a different part of the body than the fingertip of the user, such as a finger or palm (a part of the body where blood flow can be readily observed).

As described above, the safety management system S in this embodiment can permit or prohibit operation by controlling the motive power of the transportation machine. The safety management system S includes the driver authentication section 11 which authenticates the driver of the transportation machine and outputs an authentication result, the health status determination section 12 which measures the blood component data of the driver authenticated by the driver authentication section 11, determines the health status of the driver from the blood component data, and outputs a determination result, and the motive power control section 13 which permits or prohibits operation of the transportation machine by controlling motive power of the transportation machine based on the authentication result and the determination result.

According to this configuration, a legitimate driver is authenticated. Furthermore based on the blood component data of that driver, it is determined whether or not the health status of the driver is favorable. Based on the results, operation can be permitted or prohibited by controlling starting of the engine of the transportation machine. As a result, the likelihood of occurrence of an accident due to poor health of the driver, can be reduced.

In the safety management system S, the driver authentication section 11 authenticates drivers based on a vein pattern obtained by irradiating infrared rays onto the body of the driver. Therefore, authentication can be performed with similar accuracy to authentication using fingerprint or iris recognition. In the safety management system S, the health status determination section 12 measures the blood component data of the driver based on an absorption spectrum obtained by irradiating infrared rays onto the body of the driver. Thus, because the blood component data is measured in a non-invasive manner, the physical and mental stress experienced by the driver can be minimized.

In the safety management system S, the vein pattern used by the driver authentication section 11 and the absorption spectrum used by the health status determination section 12 are detected by a single sensor section 14. As a result, driver authentication and health status determination can be performed in the same operation, and the structure of the overall system can be simplified. The present invention is not limited to the embodiment described above. For example, the health status determination section 12 may adopt the following configuration. That is to say, the health status determination section 12 assigns a predetermined range as the normal range for each item of the retrieved blood component data including those not designated as the specific items. The health status determination section 12 determines whether the values of all items including the specific items in the measured blood component data are within the predetermined ranges defined for each item in the retrieved blood component data. From the judgment results, the health status determination section 12 determines that the health status of the user is suitable for operating the transportation machines when the values of all items are within their predetermined ranges or when the number of items within their predetermined ranges is equal to or greater than a predetermined number. In addition, based on the judgment results, the motive power control section 13 controls the motive power to permit operation of the transportation machine. At this time, a requirement may be that the values of all of the specific items are within their predetermined ranges.

A log creation section may be provided which creates logs of such information as the identity and health status of the driver, and the date and time. At this time, the log creation section may be connected for example to a navigation system installed in a standard vehicle, and some or all of the log information may be displayed on a screen. Log information may be displayed as numerical data, or in the form of a graph or the like. As a result, the driver can monitor his or her health status on a daily basis.

If data that cannot be read by the sensor section 14 (such as the breath alcohol concentration of the driver) is to be used as a condition for controlling motive power, a detection device for obtaining the data can be incorporated into the safety management system, and the motive power controlled in light of this additional data.

The blood component data may also be obtained by collecting a blood sample.

The construction of the embodiment described above is but one example of the present invention, and various modifications are possible provided that they do not depart from the scope of the present invention.

What is claimed is:

1. A safety management system comprising:
a sensor section to irradiate infrared light onto a portion of skin of a driver of a transportation machine, receive the light passed through the portion of the skin of the driver, and acquire, from the received light, optical information related to a vein pattern of the portion of the skin of the driver and blood component data of the driver including a plasma protein level, a lactic acid level, a blood sugar level and an enzyme level;
a driver authentication section to obtain the vein pattern from the optical information, to authenticate the driver of the transportation machine based on the vein pattern and to output an authentication result;
a health status determination section to measure the blood component data of the driver authenticated by said driver authentication section from the optical information, said health status determining section being configured to determine whether or not values of the plasma protein level and the lactic acid level in the blood component data measured by said health status determination section are within pre-registered blood component data values indicating an appropriate health status including a level of tiredness of the driver for operating the transportation machine, and to output a determination result, wherein the health status determination section is configured to correct ranges of the pre-registered blood component data values based on previously acquired blood component data of said driver; and
a motive power control section to permit or prohibit operation of the transportation machine by controlling motive power of the transportation machine based on the authentication result, the determination result and the level of tiredness of the driver.

2. A safety management system according to claim 1, wherein said motive power control section controls starting of an engine of the transportation machine, based on the authentication result, the determination result and the level of tiredness of the driver.

3. A safety management system according to claim 1, wherein the health status determination section is adapted to measure said blood component data, including the plasma protein level and the lactic acid level, via a surface of the driver's fingertip in use.

4. A safety management system according to claim 1, wherein the blood component data includes said plasma protein level, said lactic acid level, said blood sugar level, said enzyme level and a cholesterol level.

5. A safety management system according to claim 1, wherein the health status determination section varies the pre-registered blood component data values according to characteristics of the driver.

6. A safety management system according to claim 1, wherein the health status determination section establishes the pre-registered blood component data values based on age and gender of the driver.

7. A safety management system comprising:
a sensor section to irradiate infrared light onto a portion of skin of a driver of a transportation machine, receive the light passed through the portion of the skin of the driver, and acquire, from the received light, optical information related to a vein pattern of the portion of the skin of the driver and pre-designated specific items of blood component data of the driver, the specific items including a plasma protein level and a lactic acid level;
a driver authentication section to obtain the vein pattern from the optical information, to authenticate the driver of the transportation machine based on the vein pattern and to output an authentication result;
a health status determination section to measure the blood component data of the driver authenticated by said driver authentication section from the optical information, said health status determining section being configured to determine whether or not values of the plasma protein level and the lactic acid level in the blood component data measured by said health status determination section are within pre-registered blood component data values indicating an appropriate health status including a level of tiredness of the driver for operating the transportation machine, and to output a determination result, wherein the health status determination section is configured to correct ranges of the pre-registered blood component data values based on previously acquired blood component data of said driver; and a motive power control section to permit or prohibit operation of the transportation machine by controlling motive power of the transportation machine based on the authentication result, the determination result and the level of tiredness.

* * * * *